United States Patent [19]

McCormack et al.

[11] 4,263,911

[45] Apr. 28, 1981

[54] HAND ACTUATED MEDICAL SUCTION APPARATUS

[75] Inventors: Carl W. McCormack, Dallas; Roy W. Ferrell, Garland, both of Tex.

[73] Assignee: Emergency Medical Devices, Inc., Dallas, Tex.

[21] Appl. No.: 10,215

[22] Filed: Feb. 8, 1979

[51] Int. Cl.³ ............................................. A61M 1/00
[52] U.S. Cl. .............................. 128/276; 128/218 PA; 128/297
[58] Field of Search ...................... 141/65; 222/47, 49, 222/50; 128/273, 276, 277, 278, 215, 218 C, 218 PA, 234, 348, 297

[56] References Cited

U.S. PATENT DOCUMENTS

| | | | |
|---|---|---|---|
| 1,221,103 | 4/1917 | Sorensen | 128/297 |
| 2,541,402 | 2/1951 | Caine | 128/351 |
| 3,040,744 | 6/1962 | Hoggard | 128/218 C |
| 3,375,828 | 4/1968 | Sheridan | 128/351 |
| 3,435,826 | 4/1969 | Fogarty | 128/348 |
| 3,625,221 | 12/1971 | Corbett | 128/351 |
| 3,828,781 | 8/1974 | Rothman | 128/278 |
| 3,863,635 | 2/1975 | Swatman | 128/276 |
| 3,937,220 | 2/1976 | Coyne | 128/276 |
| 3,993,064 | 11/1976 | McCarthy et al. | 128/218 PA |
| 4,036,232 | 7/1977 | Genese | 128/278 |
| 4,114,625 | 9/1978 | Onat | 128/348 |

OTHER PUBLICATIONS

Webster's Seventh New Collegiate Dictionary, G&C Merriam Co., Springfield, Mass., 1963, p. 895 "Syringe".

Primary Examiner—Robert W. Michell
Assistant Examiner—J. L. Kruter
Attorney, Agent, or Firm—W. Thomas Timmons

[57] ABSTRACT

A hand actuated medical suction apparatus especially suited for aspirating vomitus from the airway of an unconscious person in emergency field operations is disclosed. The apparatus includes a cylinder for containing the evacuated vomitus, a piston movable within the cylinder, forming a substantially airtight seal with the wall of the cylinder, and a flexible tube in communication with the cylinder. The apparatus also includes a smooth convex surface forming a tip for the distal end of the flexible tube. The flexible tube forms at least one aperture in the distal end near the smooth convex surface. In one arrangement of the apparatus, the piston can be moved by a trigger which is longitudinally slidable along the outside of the cylinder, a linkage for transmitting motion from the trigger to the piston, and a grip affixed to the cylinder near the end of the cylinder opposite the tube end and extending outward from the cylinder in the same direction as the trigger. The grip and the trigger are adapted to be gripped by one hand of a medical worker so that the apparatus can be operated with one hand. The linkage includes a piston rod connected to the piston and a trigger link connecting the trigger to the end of the piston rod distal to the piston for transmitting motion from the trigger to the piston rod. Another arrangement of the apparatus includes a hand actuated syringe for containing the aspirated vomitus, and an endotracheal tube in communication with the syringe for insertion into the unconscious person's airway.

2 Claims, 7 Drawing Figures

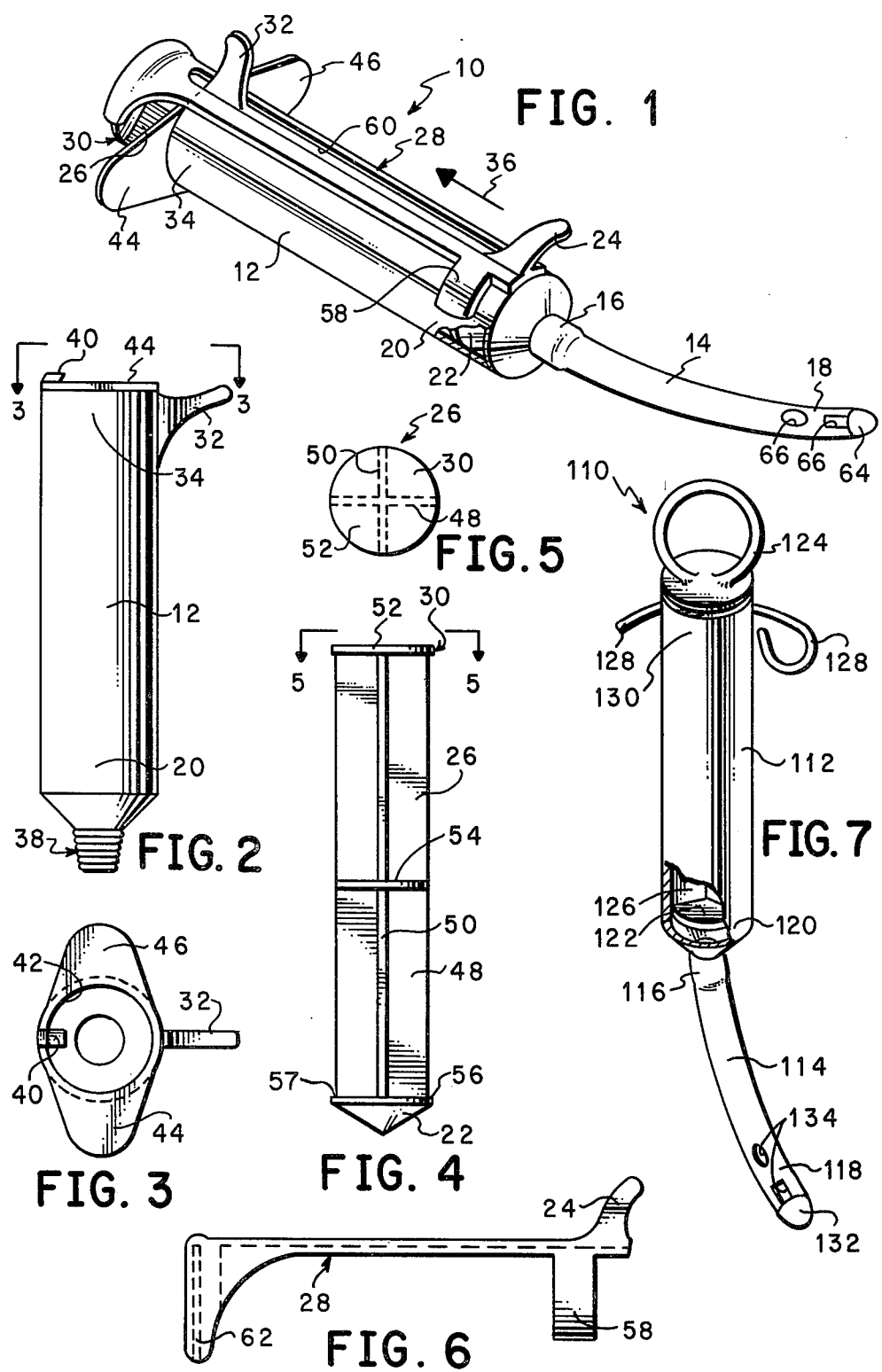

HAND ACTUATED MEDICAL SUCTION APPARATUS

BACKGROUND OF THE INVENTION

1. Field of the Invention

The present invention relates generally to emergency medical equipment, and in one of its aspects, to a medical suction apparatus.

2. Description of the Prior Art

In emergency field operations, emergency medical technicians need a suction device to aspirate vomitus from the airways of unconscious patients. The suction device which is currently most common in the field is the Laerdal Jet Suction apparatus. The Laerdal Jet Suction apparatus creates a suction effect by passing freon across a venturi tube. The apparatus is bulky, requires set-up time, has a limited operating time, and becomes very cold during operation, possibly causing cold burns to the patient.

U.S. Pat. No. 3,375,828, issued to Sheridan, U.S. Pat. No. 3,625,221, issued to Corbett, and U.S. Pat. No. 3,863,635, issued to Swatman, all show the use of suction devices that allow hand adjustment of the amount of suction pressure, but the devices shown in all three patents are designed to be used with conventional suction devices such as suction pumps. None of the suction devices shown in these patents are especially adapted to field operation.

SUMMARY OF THE INVENTION

It is therefore an object of the present invention to provide a suction apparatus especially suited for emergency field operation.

It is another object of the present invention to provide a medical suction apparatus which is easily portable.

It is yet another object of the present invention to provide a medical suction apparatus which can be used for one-hand operation.

A further object of the present invention is to provide a medical suction apparatus of adequate volume which is non-injurious to patients.

A hand actuated medical suction apparatus according to the present invention includes a cylinder, a piston movable within the cylinder, a hand actuated means for moving the piston within the cylinder, and a flexible tube in communication with the cylinder, having a proximal end and a distal end, with the proximal end attached to one end of the cylinder. The piston forms a substantially airtight seal with the wall of the cylinder. A preferred form of the apparatus also includes a smooth convex surface forming a tip for the distal end of the flexible tube. In such an arrangement, the flexible tube forms at least one aperture in the distal end near the smooth convex surface.

A preferred arrangement of the hand actuated means for moving the piston within the cylinder includes a trigger longitudinally slidable along the outside of the cylinder, a linkage for transmitting motion from the trigger to the piston, and a grip affixed to the cylinder near the end of the cylinder opposite the tube end and extending outward from the cylinder in the same direction as the trigger. The trigger is proximal to the tube end of the cylinder when the piston is proximal to the tube end of the cylinder, and the piston is moved away from the tube end of the cylinder by moving the trigger longitudinally along the exterior of the cylinder away from the tube end of the cylinder. The grip and the trigger are adapted to be gripped by one hand of a medical worker such as a doctor, nurse, or paramedic so that the piston is moved away from the tube end of the cylinder by the medical worker by pulling the trigger toward the grip, allowing the medical suction apparatus to be actuated by one hand. One form of the linkage includes a piston rod connected to the piston and a trigger link connecting the trigger to the end of the piston rod which is distal to the piston for transmitting motion from the trigger to the piston rod. The trigger link includes means for slidably engaging the cylinder. The trigger link forms an elongated opening longitudinal to the cylinder fitting over the grip so that the grip acts as a guide for the movement of the trigger link.

Another arrangement of the hand actuated medical suction apparatus which is suitable for aspirating vomitus from the airway of an unconscious person, includes a hand actuated syringe of sufficient capacity to contain a significant amount of the vomitus from the airway of the person, and an endotracheal tube in communication with the syringe having a proximal end and a distal end, with the proximal end attached to one end of the cylinder. The endotracheal tube is long enough to reach from the syringe outside of the person's mouth into the person's airway.

These and other objects, advantages and features of this invention will be apparent from the following description taken with reference to the accompanying drawings, wherein is shown the preferred embodiments of the invention.

BRIEF DESCRIPTION OF THE DRAWINGS

FIG. 1 is a perspective view of a hand actuated medical suction apparatus according to the present invention;

FIG. 2 is an elevation view of a cylinder and a grip of the apparatus of FIG. 1;

FIG. 3 is a view of the cylinder and grip taken along lines 3—3 of FIG. 2;

FIG. 4 is an elevation view of a piston and piston rod for the hand actuated medical suction apparatus of FIG. 1;

FIG. 5 is a view of the piston and piston rod taken at 5—5 of FIG. 4;

FIG. 6 is an elevation view turned 90 degrees of a trigger and trigger link of the hand operated medical suction unit of FIG. 1; and FIG. 7 is an isometric view of an alternative embodiment of a hand actuated medical suction apparatus in accordance with the present invention.

DETAILED DESCRIPTION

Referring now to the drawings, a hand actuated medical suction apparatus according to the present invention is referred to generally by reference numeral 10 in FIG. 1. Hand actuated medical suction apparatus 10 includes a cylinder 12, and a flexible tube 14 in communication with cylinder 12. Flexible tube 14 has a proximal end 16 and a distal end 18, with proximal end 16 attached to one end 20 of cylinder 12. Hand actuated medical suction apparatus 10 also includes a piston 22 movable within cylinder 12, a trigger 24 longitudinally slidable along the outside of cylinder 12, a piston rod 26 connected to piston 22, and a trigger link 28 connecting trigger 24 to end 30 of piston rod 26 distal to piston 22 for transmitting motion from trigger 24 to piston rod 26.

Piston rod 26 combined with trigger link 28 forms a linkage for transmitting motion from trigger 24 to piston 22, and the linkage for transmitting motion from trigger 24 to piston 22 combined with trigger 24 is one hand actuated means for moving piston 22 within cylinder 12. Piston 22 forms a substantially airtight seal with the wall of cylinder 12.

Referring now to FIGS. 1 and 2, hand actuated medical suction apparatus 10 further includes a grip 32 affixed to cylinder 12 near end 34 of cylinder 12 opposite tube end 20 and extending outward from cylinder 12 in the same direction as trigger 24. Grip 32 and trigger 24 are adapted to be gripped by one hand of a medical worker so that piston 22 is moved away from tube end 20 of cylinder 12 by the medical worker by pulling trigger 24 toward grip 32, which is in the direction 36, allowing medical suction apparatus 10 to be actuated by one hand. Referring particularly to FIG. 2, one embodiment of cylinder 12 includes one-way ridges 38 forming a tip of tube end 20 for holding flexible tube 14. Medical suction apparatus 10 also includes a piston stop 40 affixed to the opening 42 in end 34 of cylinder 12. Piston stop 40 stops the movement of piston 22 in the direction 36, preventing piston 22 from exiting cylinder 12 through opening 42. Medical suction apparatus 10 further includes lateral fins 44 and 46 affixed to end 34 of cylinder 12, extending away from cylinder 12 at substantially right angles to grip 32. Lateral fins 44 and 46 serve as additional hand grips when necessary, but also serve to stop the longitudinal motion of trigger link 28 both when piston 22 is fully inserted into cylinder 12 and when it is nearly removed from cylinder 12.

Referring now to FIGS. 4 and 5, piston rod 26 can be a conventional piston rod, but in the present example is made of a special lightweight but sturdy construction comprising longitudinal cross pieces 48 and 50 supported by lateral supports 52, 54, and 56. Lateral support 56 is circumferentially surrounded by a rubber ring 57 as part of piston 22 to ensure that a substantially airtight seal is formed between piston 22 and the wall of cylinder 12.

Referring now to FIGS. 1 and 6, trigger link 28 includes means 58 for slidably engaging cylinder 12. In the embodiment shown, means 58 comprises a pair of opposing guide fingers which are annular with respect to cylinder 12, only one of which is visible in the figures. Trigger link 28 forms an elongated opening 60 longitudinal to cylinder 12 fitting over grip 32 so that grip 32 acts as a guide for the movement of trigger link 28 in the direction 36. Trigger link 28 also forms a slot 62 for receiving end 30 of piston rod 26 for transmitting motion from trigger link 28 to piston rod 26.

Hand actuated medical suction apparatus 10 further includes a smooth convex surface 64 forming a tip for distal end 18 of flexible tube 14. Flexible tube 14 forms at least one aperture 66 in distal end 18 near smooth convex surface 64. When used for removing vomitus from the airway of a person, tube 14 is inserted through the person's mouth until at least one aperture 66 is in the airway. Smooth convex surface 64 prevents damaging the soft tissue of the mouth and airway, and having more than one aperture near the smooth convex surface prevents the end of the tube from sucking up against the inside of the mouth or airway.

Referring now to FIG. 7, an alternative embodiment of a hand actuated medical suction apparatus according to the present invention is referred to generally by reference numeral 110. Hand actuated medical suction apparatus 110 includes a hand actuated syringe 112 of sufficient capacity to contain a significant amount of the vomitus from the airway of a person, and an endotracheal tube 114 in communication with syringe 112 for transferring the vomitus from the airway to the syringe. Endotracheal tube 114 has a proximal end 116 and a distal end 118 attached to one end 120 of syringe 112. Endotracheal tube 114, in order to be used for aspirating vomitus from the airway of an unconscious person, is long enough to reach from syringe 112 which is outside of the person's mouth into the person's airway.

Syringe 112 includes a piston 122 movable within the syringe cylinder, a handle 124, and a piston rod 126 connected between piston 122 and handle 124 for transmitting motion from handle 124 to piston 122. Syringe 112 also includes at least one grip 128 affixed to end 130 of syringe 112 which is opposite to tube end 120.

Hand actuated medical suction apparatus 110 further includes a smooth convex surface 132 forming a tip for distal end 118 of endotracheal tube 114. Endotracheal tube 114 forms at least one aperture 134 in distal end 118 near smooth convex surface 132.

The medical suction apparatus of this invention thus uses positive displacement suction rather than a venturi-type suction. A cylinder or syringe of 60 cubic centimeters in volume is adequate to remove vomitus from the airway of a large adult. Should the flexible tube become blocked, it can quickly and easily be cleared by pushing on the piston. The hand actuated medical suction apparatus of this invention does not compete significantly with the patient's air for breathing. Hand actuated medical suction apparatus 10 can be operated with one hand, thus freeing the other hand of an emergency medical worker. A medical suction apparatus according to the present invention is easily cleaned by simply dismantling the apparatus. The apparatus is quickly disassembled and reassembled in possible emergency situations. An apparatus according to the present invention is easily carried in most first aid kits, and can be conveniently broken down into two parts: the syringe or cylinder, and the tube. The hand actuated medical suction apparatus can be carried in a disposable plastic emesis basin. The basin can then be used to empty the suction device.

From the foregoing it will be seen that this invention is one well adapted to attain all of the ends and objects hereinabove set forth, together with other advantages which are obvious and which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

The invention having been described, what is claimed is:

1. A hand actuated medical suction apparatus comprising in combination:
   a cylinder;
   a piston movable within the cylinder, forming a substantially airtight seal with the wall of the cylinder;
   a flexible tube in communication with the cylinder, having a proximal end and a distal end, with the proximal end attached to one end of the cylinder;

a trigger extending outwardly from the cylinder in a substantially radial direction, longitudinally slidable along the outside of the cylinder;

a linkage for transmitting motion from the trigger to the piston wherein the trigger is proximal to the tube end of the cylinder when the piston is proximal to the tube end of the cylinder, and the piston is moved away from the tube end of the cylinder by moving the trigger longitudinally along the exterior of the cylinder away from the tube end of the cylinder; and a grip affixed to the cylinder near the end of the cylinder opposite the tube end and extending outwardly from the cylinder in the same direction as the trigger wherein the grip and the trigger are adapted to be gripped by one hand of a medical worker whereby the piston is moved away from the tube end of the cylinder by the medical personnel by pulling the trigger toward the grip, allowing the medical suction apparatus to be actuated by one hand;

wherein the linkage for transmitting motion from the trigger to the piston comprises in combination:

a piston rod connected to the piston; and a trigger link connecting the trigger to the end of the piston rod distal to the piston for transmitting motion from the trigger to the piston rod, including means for slidably engaging the cylinder, wherein the trigger link forms an elongated opening longitudinal to the cylinder fitting over the grip whereby the grip acts as a guide for the movement of the trigger link.

2. A hand actuated medical suction apparatus according to claim 1 further comprising a smooth convex surface forming a tip for the distal end of the flexible tube, wherein the flexible tube forms at least one aperture in the distal end near the smooth convex surface.

* * * * *